United States Patent
Kimura (10) Patent No.: US 10,653,306 B2
(45) Date of Patent: May 19, 2020

(54) ELECTRONIC CIRCUIT UNIT, IMAGING UNIT, AND ENDOSCOPE

(71) Applicant: OLYMPUS CORPORATION, Tokyo (JP)

(72) Inventor: Hiroyuki Kimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/358,938

(22) Filed: Mar. 20, 2019

(65) Prior Publication Data

US 2019/0216304 A1    Jul. 18, 2019

Related U.S. Application Data

(63) Continuation of application No. PCT/JP2017/041903, filed on Nov. 21, 2017.

(30) Foreign Application Priority Data

Dec. 5, 2016    (JP) .................................. 2016-235802

(51) Int. Cl.
*H01B 1/04*    (2006.01)
*A61B 1/05*    (2006.01)
(Continued)

(52) U.S. Cl.
CPC ............ *A61B 1/051* (2013.01); *A61B 1/0011* (2013.01); *A61B 1/00114* (2013.01);
(Continued)

(58) Field of Classification Search
CPC ... A61B 1/051; A61B 1/0011; A61B 1/00124; A61B 1/00114; H01B 7/0009;
(Continued)

(56) References Cited

U.S. PATENT DOCUMENTS

| | | | |
|---|---|---|---|
| 2004/0029454 A1 | 2/2004 | Onuma et al. | |
| 2012/0083415 A1* | 4/2012 | Tanaka | H01L 39/2487 505/431 |
| 2013/0050457 A1* | 2/2013 | Murayama | A61B 1/0008 348/75 |
| 2015/0157189 A1* | 6/2015 | Shimada | A61B 1/00071 600/137 |

(Continued)

FOREIGN PATENT DOCUMENTS

| | | |
|---|---|---|
| JP | H04-235475 A | 8/1992 |
| JP | H09-082447 A | 3/1997 |

(Continued)

OTHER PUBLICATIONS

International Search Report dated Feb. 27, 2018 issued in PCT/JP2017/041903.

(Continued)

*Primary Examiner* — Howard D Brown, Jr.
(74) *Attorney, Agent, or Firm* — Scully, Scott, Murphy & Presser, P.C.

(57) ABSTRACT

An electronic circuit unit includes: a cable having a core of stranded thin wires, the core being covered with an outer surface, the outer surface at one end of the cable being removed to expose the core; a metallic tube that is tubular, the exposed core being inserted into an opening portion of the metallic tube; and a substrate including a connection land for connecting the core. The exposed core is connected to the connection land via the metallic tube by diffusion joining or ultrasound joining, the core has a diameter of 0.02 to 0.50 mm, the metallic tube has a thickness of 10 to 50 μm, and the metallic tube has an inner diameter that is larger than the diameter of the core by equal to or more than 1.1-fold and equal to or less than by 1.5-fold.

11 Claims, 11 Drawing Sheets

(51) Int. Cl.
*H01B 7/00* (2006.01)
*H01B 7/20* (2006.01)
*H05K 1/18* (2006.01)
*H05K 1/14* (2006.01)
*H04N 5/225* (2006.01)
*A61B 1/00* (2006.01)
*G02B 23/24* (2006.01)
*H01R 4/00* (2006.01)
*H01R 43/02* (2006.01)
*H01R 4/02* (2006.01)

(52) U.S. Cl.
CPC .......... *A61B 1/00124* (2013.01); *G02B 23/24* (2013.01); *H01B 7/0009* (2013.01); *H01B 7/20* (2013.01); *H01R 4/00* (2013.01); *H04N 5/2251* (2013.01); *H05K 1/147* (2013.01); *H05K 1/189* (2013.01); *H01R 4/023* (2013.01); *H01R 43/0207* (2013.01); *H01R 2201/12* (2013.01); *H04N 2005/2255* (2013.01); *H05K 2201/10121* (2013.01); *H05K 2201/10151* (2013.01); *H05K 2201/10356* (2013.01); *H05K 2201/10734* (2013.01)

(58) Field of Classification Search
CPC .. H01B 7/20; H01R 43/0207; H01R 2201/12; H01R 4/023; H01R 4/00; H04N 2005/2255; H04N 5/2251; H05K 2201/10121; H05K 2201/10151; H05K 2201/10356; H05K 2201/10734; H05K 1/189; H05K 1/147; G02B 23/2484; G02B 23/24
See application file for complete search history.

(56) References Cited

U.S. PATENT DOCUMENTS

| | | | |
|---|---|---|---|
| 2015/0335230 A1* | 11/2015 | Tomatsu | A61B 1/045 600/109 |
| 2016/0029879 A1 | 2/2016 | Ishikawa | |
| 2017/0127921 A1 | 5/2017 | Motohara et al. | |
| 2018/0122529 A1* | 5/2018 | Hwang | H01B 7/0009 |
| 2018/0325360 A1* | 11/2018 | Sekido | A61B 1/00124 |

FOREIGN PATENT DOCUMENTS

| | | |
|---|---|---|
| JP | 2003-017531 A | 1/2003 |
| JP | 2003-320911 A | 11/2003 |
| JP | 2004-071372 A | 3/2004 |
| JP | 2006-298084 A | 11/2006 |
| JP | 2007-305314 A | 11/2007 |
| JP | 3163214 U | 10/2010 |
| JP | 2011-188375 A | 9/2011 |
| JP | 2013-125267 A | 6/2013 |
| JP | 2015-042219 A | 3/2015 |
| JP | 2016-083009 A | 5/2016 |
| WO | WO 2015/019671 A1 | 2/2015 |
| WO | WO 2016/092986 A1 | 6/2016 |

OTHER PUBLICATIONS

Japanese Notification of Reasons for Refusal dated Jul. 10, 2018 issued in JP2018-519995.

Nebashi, Toru et al., "COF-capable Ultrasonic Bonder, Special Edition/The Cutting Edge of Mounting-associated Equipment" (<Special Article> Frontier Technologies on "Jisso" Related Equipments), Journal of Japan institute of Electronics Packaging), 2007, vol. 10, No. 7, pp. 523-527.

* cited by examiner

ELECTRONIC CIRCUIT UNIT, IMAGING UNIT, AND ENDOSCOPE

CROSS REFERENCES TO RELATED APPLICATIONS

This application is a continuation of PCT international application Ser. No. PCT/JP2017/041903 filed on Nov. 21, 2017 which designates the United States, incorporated herein by reference, and which claims the benefit of priority from Japanese Patent Applications No. 2016-235802, filed on Dec. 5, 2016, incorporated herein by reference.

BACKGROUND

1. Technical Field

The present disclosure relates to an electronic circuit unit, an imaging unit, and an endoscope.

2. Related Art

In the related art, endoscope systems are widely used for various types of examinations in medical fields and industrial fields. Among them, medical endoscopes are widely used as they are capable of acquiring in-vivo images within a body cavity without making an incision in a subject such as patient by inserting an elongated flexible insertion portion with an imaging element provided at its distal end into the body cavity of the subject and is further capable of making treatment by protruding a treatment tool from the distal end of the insertion portion if needed.

At the distal end of the insertion portion of this type of endoscope, an imaging unit is installed which includes an imaging element and a circuit substrate on which electronic components such as capacitor and IC chip for forming a drive circuit for the imaging element are mounted, and multiple signal cables are soldered to connection lands on the circuit substrate (for example, see Japanese Laid-open Patent Publication No. 2015-42219).

SUMMARY

In some embodiments, an electronic circuit unit includes: a cable having a core of stranded thin wires, the core being covered with an outer surface, the outer surface at one end of the cable being removed to expose the core; a metallic tube that is tubular, the exposed core being inserted into an opening portion of the metallic tube; and a substrate including a connection land for connecting the core. The exposed core is connected to the connection land via the metallic tube by diffusion joining or ultrasound joining, the core has a diameter of 0.02 to 0.50 mm, the metallic tube has a thickness of 10 to 50 μm, and the metallic tube has an inner diameter that is larger than the diameter of the core by equal to or more than 1.1-fold and equal to or less than by 1.5-fold.

In some embodiments, an imaging unit includes: an imaging element configured to receive light and conduct photoelectric conversion to generate an electric signal; and the above-mentioned electronic circuit unit.

In some embodiments, an endoscope includes an insertion portion having a distal end provided with the above-mentioned imaging unit.

The above and other features, advantages and technical and industrial significance of this disclosure will be better understood by reading the following detailed description of presently preferred embodiments of the disclosure, when considered in connection with the accompanying drawings.

DETAILED DESCRIPTION

An explanation is given below of an endoscope system including an imaging unit as an aspect (hereafter, referred to as "embodiment") for implementing the disclosure. Furthermore, the embodiment is not a limitation on the disclosure. Moreover, in description of drawings, the same components are attached with the same reference numeral. Moreover, it should be noted that the drawings are schematic and the relation between members in thickness and width, the ratio between members, and the like, are differ from reality. Moreover, each of the drawings contains parts that are different in dimension or proportion.

First Embodiment

Figure 1:
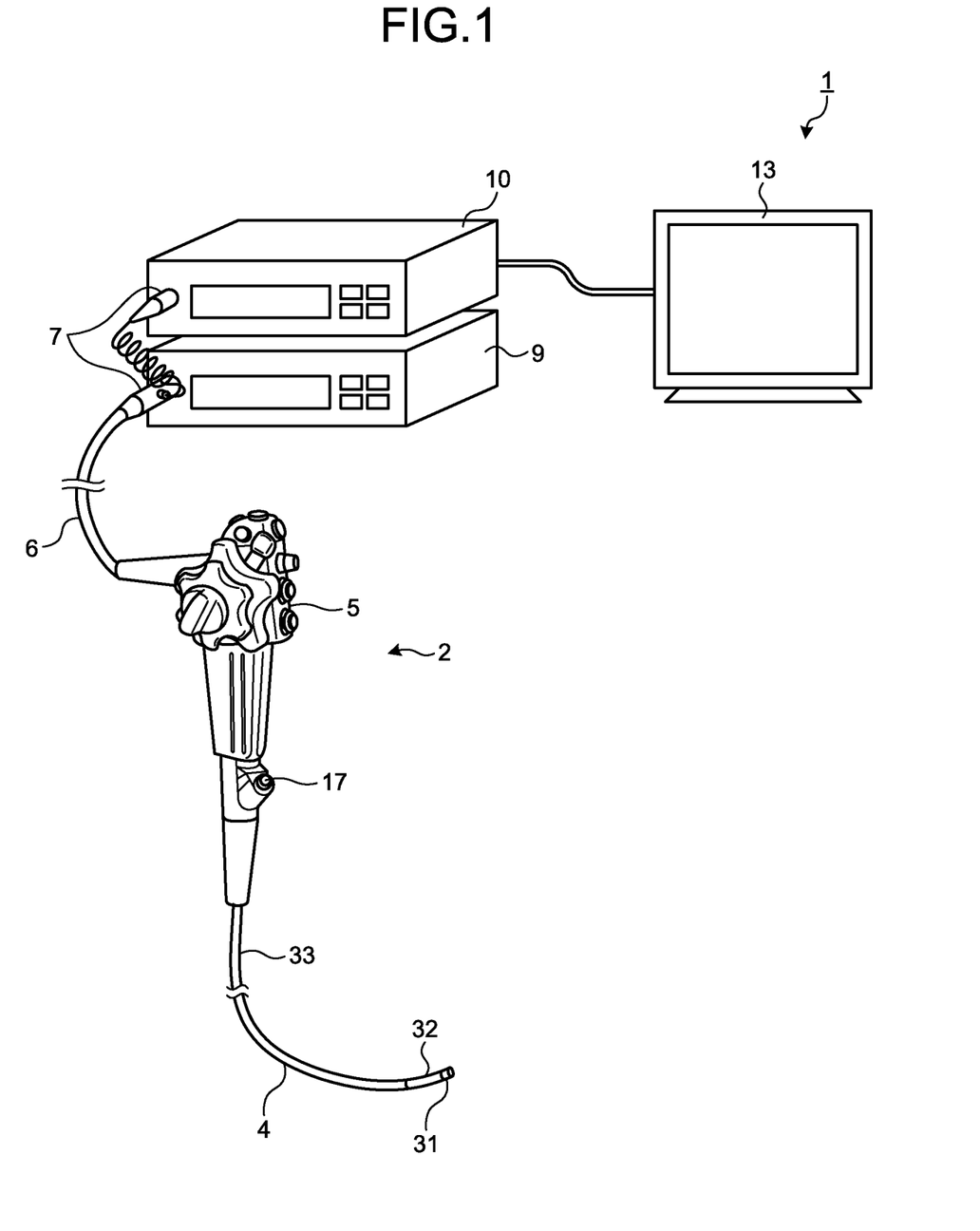
FIG. 1 is a diagram that schematically illustrates the overall configuration of an endoscope system according to a first embodiment of the disclosure.

FIG. 1 is a diagram that schematically illustrates the overall configuration of an endoscope system according to an embodiment of the disclosure. As illustrated in FIG. 1, an endoscope system 1 includes an endoscope 2, a universal code 6, a connector 7, a light source device 9, a processor (control device) 10, and a display device 13.

The endoscope 2 has an insertion portion 4 inserted into the body cavity of a subject so as to capture in-vivo images of the subject and output imaging signals. A bundle of electric cables inside the universal code 6 extends up to the distal end of the insertion portion 4 in the endoscope 2 and connects to an imaging device 35 (see FIG. 2) provided in a distal end part 31 of the insertion portion 4.

The connector 7 is provided at the proximal end of the universal code 6 and is connected to the light source device 9 and the processor 10 so that it performs predetermined signal processing on imaging signals output from the imaging device 35 in the distal end part 31 connected to the universal code 6 and conducts analog-digital conversion (A/D conversion) on imaging signals to output them as image signals.

The light source device 9 is configured by using for example a white LED. Pulsed white light emitted from the light source device 9 becomes illumination light that is passed through the connector 7 and the universal code 6 and is emitted from the distal end of the insertion portion 4 in the endoscope 2 toward an object.

The processor 10 conducts predetermined image processing on image signals output from the connector 7 and performs overall control of the endoscope system 1. The display device 13 displays image signals processed by the processor 10.

The proximal end side of the insertion portion 4 in the endoscope 2 is connected to an operating unit 5 that is provided with various types of buttons or knobs to perform endoscope functions. The operating unit 5 is provided with a treatment-tool insertion opening 17 for inserting a treatment tool, such as biopsy forceps, electric cautery, or examination probe, into the body cavity of a subject.

The insertion portion 4 is composed of the distal end part 31 in which the imaging device 35 is provided; a curved portion 32 that is continuous with the proximal end side of the distal end part 31 and is flexibly curved in multiple directions; and a flexible tube portion 33 that is continuous with the proximal end side of the curved portion 32. The curved portion 32 is curved due to operation of a curving-operation knob provided in the operating unit 5 and, in accordance with pulling and loosening of a curved wire inserted inside the insertion portion 4, is flexibly curved in four directions, e.g., upward, downward, leftward, and rightward.

The endoscope 2 is provided with a light guide bundle (not illustrated) for transmitting illumination light from the light source device 9, and an illumination lens (not illustrated) is provided at the output end of illumination light from the light guide bundle. The illumination lens is provided in the distal end part 31 of the insertion portion 4, and illumination light is emitted toward the subject.

Figure 2:
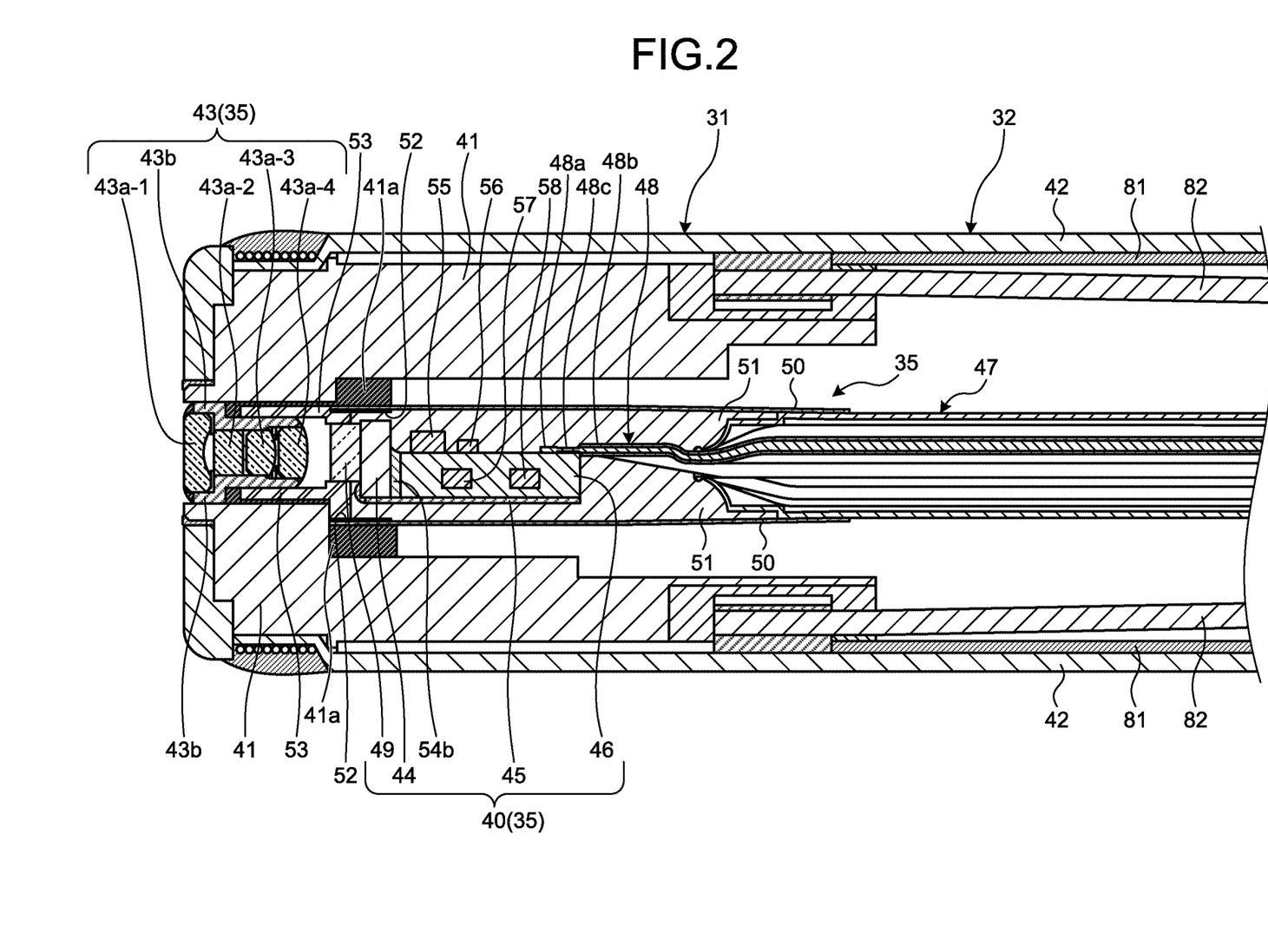
FIG. 2 is a partial cross-sectional view of the distal end of an endoscope illustrated in FIG. 1.

Next, a configuration of the distal end part 31 of the endoscope 2 is explained in detail. FIG. 2 is a partial cross-sectional view of the distal end of the endoscope 2. FIG. 2 is a cross-sectional view that is cross-section on the plane that is perpendicular to the substrate surface of the imaging device 35 provided in the distal end part 31 of the endoscope 2 and that is parallel to the optical axis direction of the imaging device 35. The distal end part 31 of the insertion portion 4 in the endoscope 2 and part of the curved portion 32 are illustrated in FIG. 2.

As illustrated in FIG. 2, the curved portion 32 is flexibly curved in four directions, upward, downward, leftward, and rightward, in accordance with pulling and loosening of a curved wire 82 that is inserted inside a curved tube 81 provided on the inner side of a cover tube 42 described later. The imaging device 35 is provided inside the distal end part 31 that extends from the distal end side of the curved portion 32.

The imaging device 35 includes a lens unit 43 and an imaging unit 40 provided on the proximal end side of the lens unit 43, and it is glued to the inner side of a distal-end main body 41 with an adhesive agent 41*a*. The distal-end main body 41 is made of a hard material for forming an inner space to accommodate the imaging device 35. The proximal-end outer circumference of the distal-end main body 41 is covered with the soft cover tube 42. A member on the proximal end side of the distal-end main body 41 is made of a soft material so that the curved portion 32 may be curved. The distal end part 31 in which the distal-end main body 41 is provided is a hard part of the insertion portion 4.

The lens unit 43 includes objective lenses 43*a*-1 to 43*a*-4 and a lens holder 43*b* that holds the objective lenses 43*a*-1 to 43*a*-4, and the distal end of the lens holder 43*b* is inserted and fitted into the inner side of the distal-end main body 41 so as to be fixed to the distal-end main body 41.

The imaging unit 40 includes an imaging element 44 such as CCD or CMOS that receives light and conducts photoelectric conversion to generate electric signals; a circuit substrate 45 that is a flexible printed substrate (hereafter, referred to as "FPC substrate") extending from the imaging element 44 in the optical axis direction; a multi-layer substrate 46 including conductor layers formed on the surface of the circuit substrate 45; and a cover glass 49 attached to the imaging element 44 in a state where it covers the light receiving surface of the imaging element 44. In the multi-layer substrate 46 of the imaging unit 40, electronic components 55 to 58 constituting a drive circuit of the imaging element 44 are mounted or built in, and vias (not illustrated) for electrically connecting the conductor layers are formed. Furthermore, a core 48*a* of each signal cable 48 in a bundle of electric cables 47 is connected, via a metallic tube 48*c*, to a connection land 63 (see FIG. 3) formed at the proximal end of the multi-layer substrate 46. Furthermore, the electronic components 55 to 58 mounted on the multi-layer substrate 46 may be other than electronic components constituting the drive circuit of the imaging element 44.

The proximal end of the signal cable 48 extends in a direction toward the proximal end of the insertion portion 4. The bundle of electric cables 47 is inserted into and provided in the insertion portion 4, and it extends up to the connector 7 via the operating unit 5 and the universal code 6 illustrated in FIG. 1.

Object images formed by the objective lenses 43*a*-1 to 43*a*-4 of the lens unit 43 are detected by the imaging element 44 provided at the image location of the objective lenses 43*a*-1 to 43*a*-4 and are converted into imaging signals. Imaging signals are output to the processor 10 through the signal cable 48 connected to the circuit substrate 45 and the multi-layer substrate 46 and the connector 7.

The imaging element 44 is attached to the circuit substrate 45 and the multi-layer substrate 46 with an adhesive agent 54*b*. The imaging element 44 and the part connecting the imaging element 44 and the circuit substrate 45 are covered with a metallic reinforcement member 52. To prevent effects of external static electricity on the electronic components 55 to 58 on the circuit substrate 45, the reinforcement member 52 is located away from the imaging element 44, the circuit substrate 45, and the multi-layer substrate 46.

The outer circumferences of the imaging unit 40 and the distal end part of the bundle of electric cables 47 are covered with a heat shrinkable tube 50 to improve tolerance. Inside the heat shrinkable tube 50, a clearance between components is filled with adhesive resin 51.

An imaging-element holder 53 holds the imaging element 44 attached to the cover glass 49 as the outer circumference of the cover glass 49 is engaged with the inner circumference of the imaging-element holder 53 on the proximal end side. The outer circumference of the imaging-element holder 53 on the proximal end side is engaged with the inner circumference of the reinforcement member 52 on the distal end side. The outer circumference of the lens holder 43b on the proximal end side is engaged with the inner circumference of the imaging-element holder 53 on the distal end side. In a state where the components are engaged with each other as described above, the outer circumference of the lens holder 43b, the outer circumference of the imaging-element holder 53, and the outer circumference of the heat shrinkable tube 50 on the distal end side are secured to the inner circumference of the distal end of the distal-end main body 41 with the adhesive agent 41a.

Figure 3:
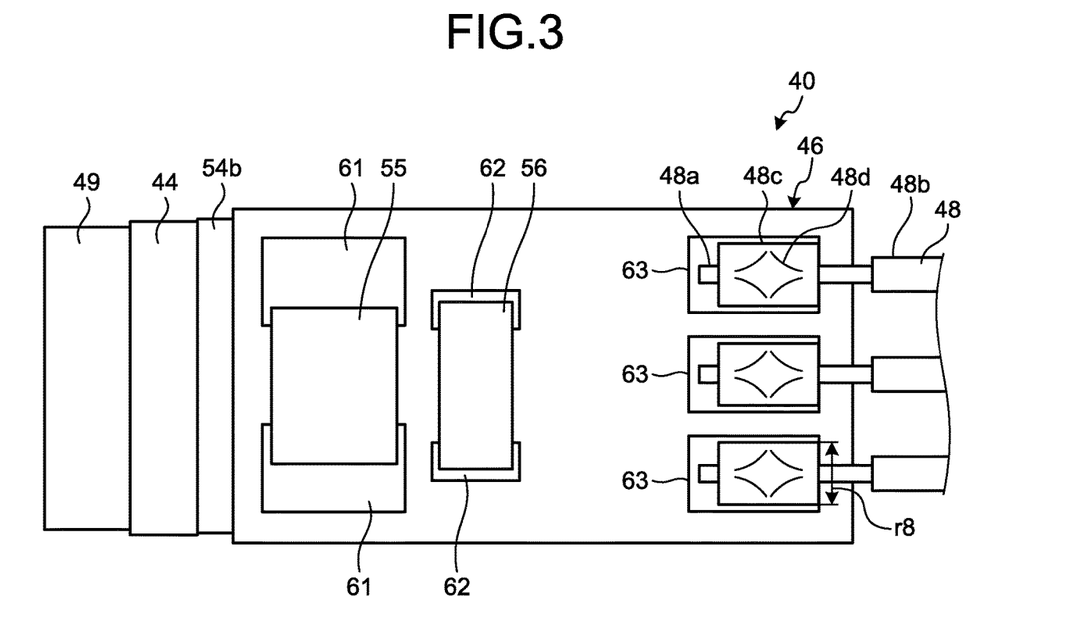
FIG. 3 is a plan view of an imaging unit illustrated in FIG. 2 when it is viewed in a planar manner in a laminating direction.
Figure 4:
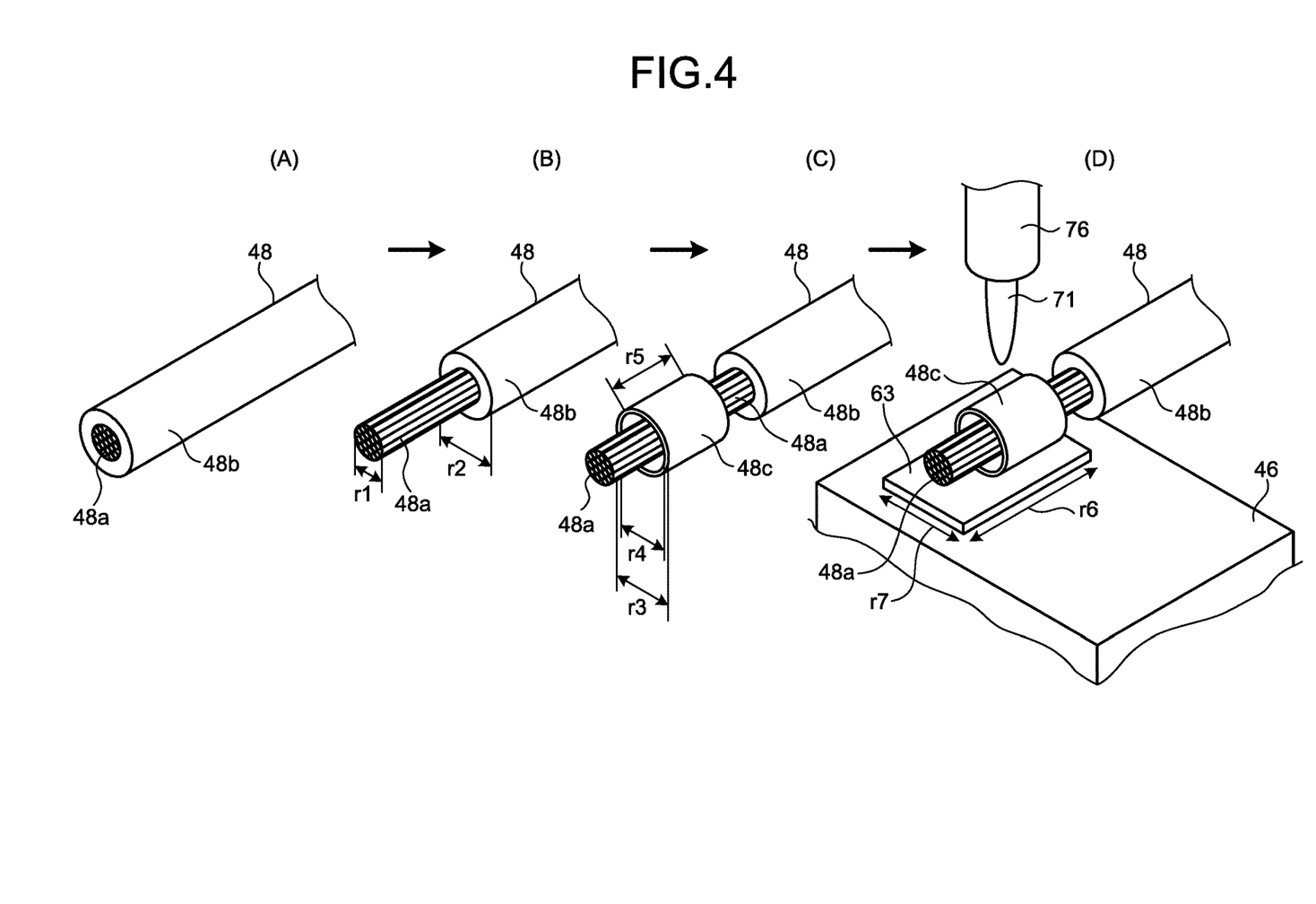
FIG. 4 is a perspective view that illustrates joining of a signal cable to a connection land.
Figure 5:
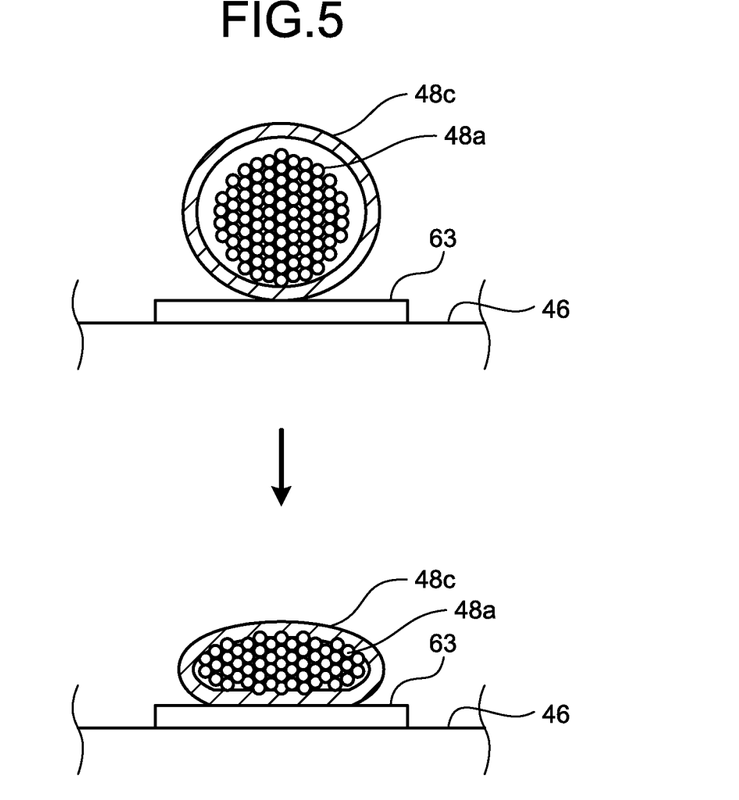
FIG. 5 is a cross-sectional view that illustrates joining of the signal cable to the connection land.

Next, the imaging unit 40 is explained. FIG. 3 is a plan view of the imaging unit 40 when it is viewed in a planar manner in a laminating direction. FIG. 4 is a perspective view that illustrates joining of the signal cable 48 to the connection land 63 of the imaging unit 40. FIG. 5 is a cross-sectional view that illustrates joining of the signal cable 48 to the connection land 63.

The multi-layer substrate 46 is provided with two connection lands 61 to which the electronic component 55 is electrically connected, two connection lands 62 to which the electronic component 56 is connected, and the connection lands 63 to which the core 48a of the signal cable 48 is electrically and mechanically connected. In the example of FIG. 3, the connection lands 63 are disposed at three areas, and the three signal cables 48 are connected via the metallic tubes 48c.

The signal cable 48 is obtained by covering the core 48a, which is stranded thin wires, with an outer surface 48b that is made of an insulating material.

The metallic tube 48c has a cylindrical shape, and it is made of a metallic material such as gold, silver, copper, zinc, or indium. The metallic tube 48c may be made of not only a single material but also multiple types of metals, e.g., lamination of gold on copper or tin on silver. The connectivity may be improved by using, as the material of the metallic tube 48c, the material identical to the material of which the connection land 63 is formed. It is preferable that, when metals are laminated in the connection land 63, the material is identical to the material of which the surface is formed. Furthermore, it is preferable that the material of the metallic tube 48c has a lower degree of hardness than that of the material of which the core 48a is formed. The use of a material with a low degree of hardness allows the core 48a to dig into the metallic tube 48c during joining and increase the contact area (see FIG. 5). In terms of the conductive property, the degree of hardness, and oxidation prevention, it is preferable that the metallic tube 48c is made of gold or coated with gold.

To connect the signal cable 48 to the connection land 63, the outer surface 48b at one end is first removed to expose the core 48a as illustrated in (A) and (B) of FIG. 4, and then the exposed core 48a is inserted into the opening portion of the metallic tube 48c as illustrated in (C) of FIG. 4.

Then, as illustrated in (D) of FIG. 4, while the core 48a, inserted into the opening portion of the metallic tube 48c, is placed on the connection land 63, a connection tool 71 of an ultrasound vibrator 76 is pressed against the metallic tube 48c to hold, together with an undepicted anvil under the multi-layer substrate 46, the connection land 63 on the multi-layer substrate 46 and the metallic tube 48c (the core 48a) and, in a pressed state, apply vibrations for ultrasound joining. After ultrasound joining, an indentation 48d produced by the connection tool 71 is formed on the metallic tube 48c.

The core 48a of the signal cable 48 for an endoscope has a diameter r1 of 0.02 to 0.50 mm, the opening portion of the metallic tube 48c has an inner diameter r4 that is larger than the diameter r1 of the core 48a by more than 1.0-fold and equal to or less than by 1.8-fold, and the metallic tube 48c has a thickness of 10 to 50 μm. The too small inner diameter r4 of the opening portion of the metallic tube 48c makes it difficult to insert the core 48a, and when it is too big, the connection lands 63 need to be disposed at a large interval, which makes it difficult to reduce the size of the imaging unit 40. Therefore, it is preferable that the inner diameter r4 of the opening portion of the metallic tube 48c is larger than the diameter r1 of the core 48a by equal to or more than 1.1-fold and equal to or less than 1.5-fold. It is preferable that an outer diameter r3 of the metallic tube 48c is equal to or less than an outer diameter r2 of the signal cable 48. The metallic tube 48c described above may be manufactured by laminating a metallic membrane on a thin wire by a plating technique and removing the thin wire.

A length r5 of the metallic tube 48c is shorter than a length r6 of the connection land 63 in the optical axis direction. According to the first embodiment, the use of ultrasound joining enables high reliability of a connection and the short lengths r6 and r7 of the connection land 63. Furthermore, it is preferable that the length r5 of the metallic tube 48c is more than the inner diameter r4 of the opening portion of the metallic tube 48c. Furthermore, it is preferable that ultrasound joining is applied to the core 48a that is exposed at the end of the metallic tube 48c. This is because the core 48a exposed at the end of the metallic tube 48c allows visual judgement on the acceptability of ultrasound joining.

According to the first embodiment, during joining, the core 48a is covered with the metallic tube 48c having a diameter larger than that of the core 48a; therefore, the target to be joined is large, and a joining task is easy. Furthermore, the metallic tube 48c prevents thin wires from being unjoined so as to avoid the occurrence of short circuits, and the like.

In the case of joining the core 48a with the connection land 63 by using solder, it takes time to melt solder, and therefore there is a high possibility that the imaging element 44, the lens unit 43, or the like, are damaged due to heat; however, according to the first embodiment of the disclosure, ultrasound joining may reduce damages to the imaging element 44, the lens unit 43, or the like, due to heat. Furthermore, in the case of joining using solder, the connection lands 63 need to be disposed at a large interval in consideration of scattering of solder and flux; however, for ultrasound joining, the pressure and the frequency of vibration to be applied are controlled so as to control a length r8 (see FIG. 3) of the metallic tube 48c in the width direction after joining, whereby the possibility of occurrence of short circuits may be reduced. It is preferable that the length r8 of the metallic tube 48c in the width direction after joining is more than the diameter r1 of the core 48a by 1.5- to 4-fold.

According to the first embodiment of the disclosure, the core 48a is joined to the connection land 63 via the metallic tube 48c during ultrasound joining; however, this is not a limitation, and the joining may be diffusion joining using heat and pressure.

Furthermore, although the cylindrical metallic tube 48c is used according to the first embodiment, it may be like an ellipse or a rectangular column.

Figure 6:
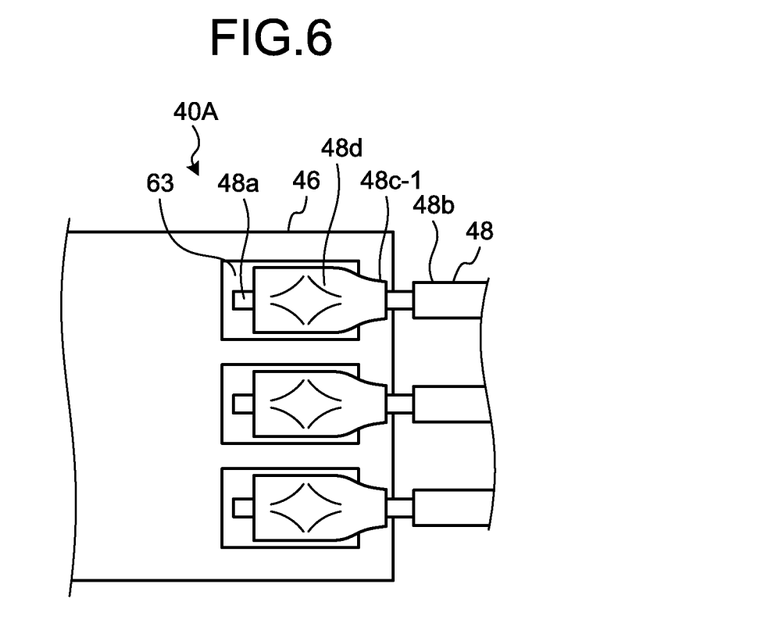
FIG. 6 is a plan view of an imaging unit according to a modification 1 of the first embodiment of the disclosure.

Furthermore, according to the first embodiment, the length r5 of the used metallic tube 48c is shorter than the length r6 of the connection land 63 in the optical axis direction; however this is not a limitation. FIG. 6 is a plan view of an imaging unit 40A according to a modification 1 of the first embodiment of the disclosure.

The imaging unit 40A uses a metallic tube 48*c*-1 whose length is longer than the length of the connection land 63 in the optical axis direction. The use of the metallic tube 48*c*-1 having a length longer than the length of the connection land 63 in the optical axis direction may protect the core 48*a*.

Figure 7:
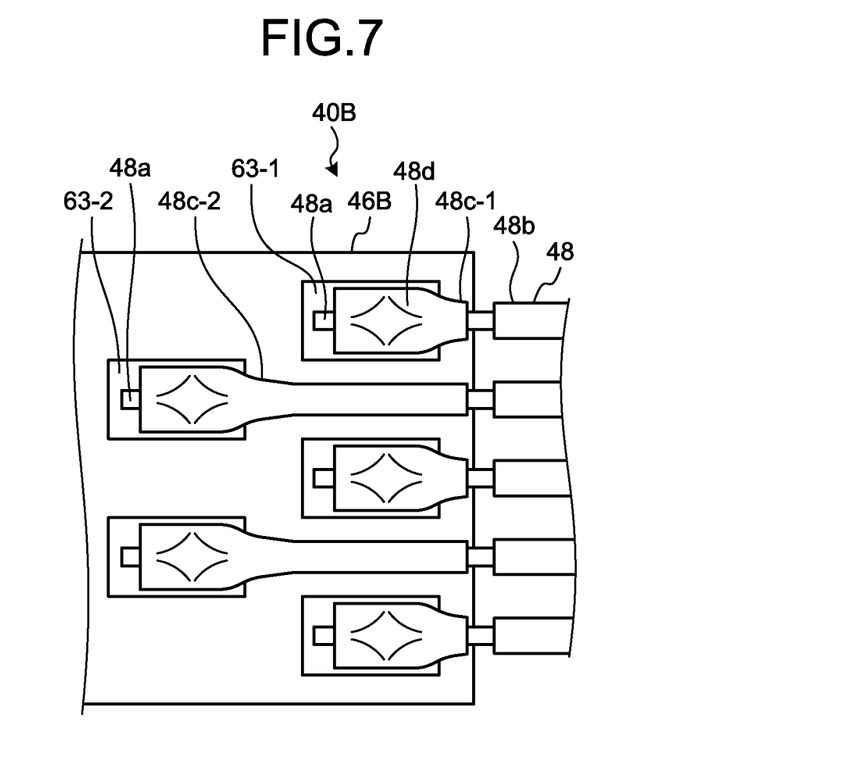
FIG. 7 is a plan view of an imaging unit according to a modification 2 of the first embodiment of the disclosure.

Further, to improve the mounting density of the signal cables 48, the connection lands 63 may be arranged in a staggered manner. FIG. 7 is a plan view of an imaging unit 40B according to a modification 2 of the first embodiment of the disclosure.

In the imaging unit 40B, the connection lands 63 (63-1, 63-2) are arranged in a staggered manner (in zigzags) on a multi-layer substrate 46B. Furthermore, the imaging unit 40B uses two types, the metallic tube 48*c*-1 and a metallic tube 48*c*-2, having different lengths. The core 48*a* of the signal cable 48 connected to the connection land 63-2 located away from the proximal end of the multi-layer substrate 46B is covered with the long metallic tube 48*c*-2, and the core 48*a* of the signal cable 48 connected to the connection land 63-1 located at the proximal end of the multi-layer substrate 46B is covered with the short metallic tube 48*c*-1.

Second Embodiment

Figure 8:
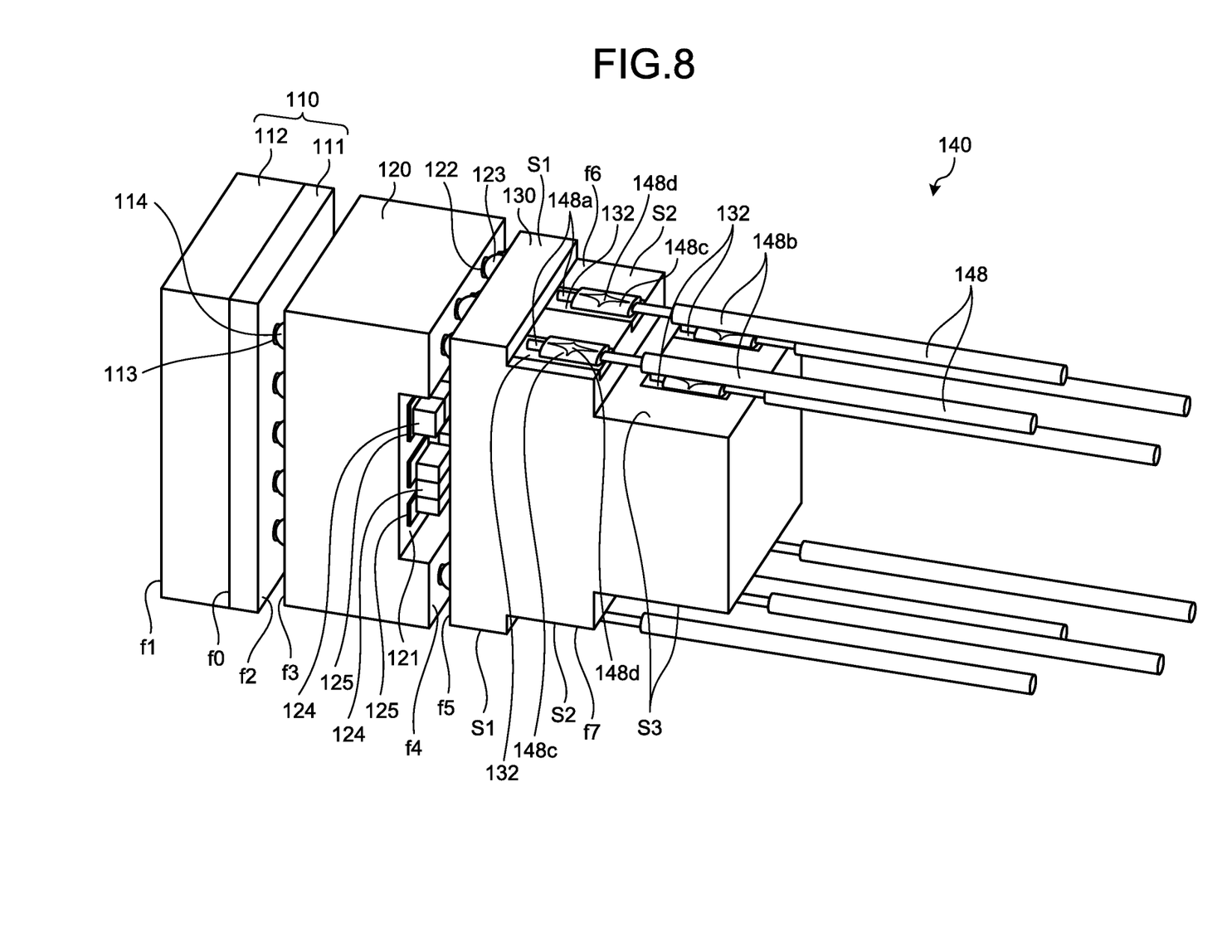
FIG. 8 is a perspective view of an imaging unit according to a second embodiment of the disclosure.
Figure 9:
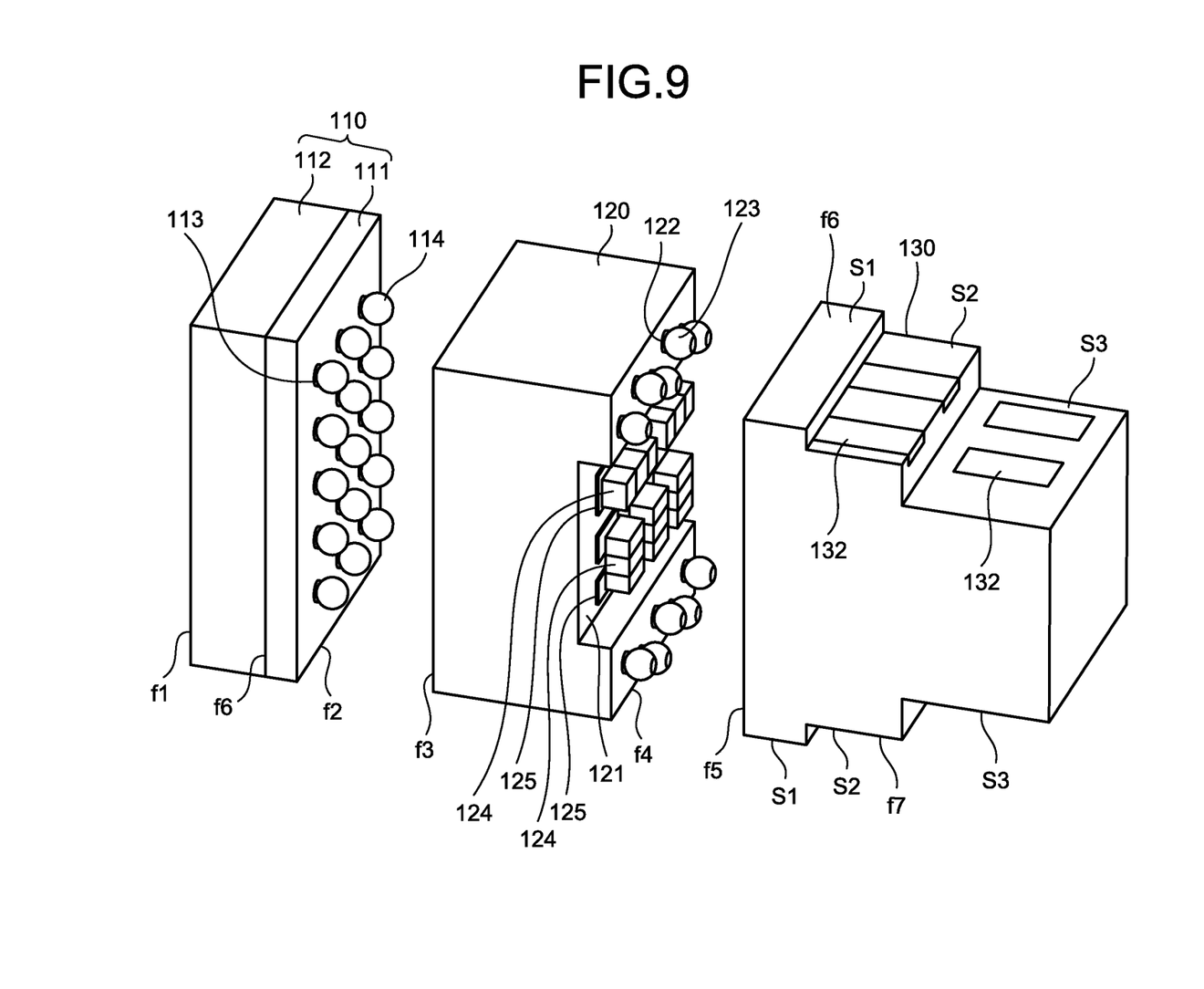
FIG. 9 is an exploded perspective view of the imaging unit of FIG. 8.
Figure 10:
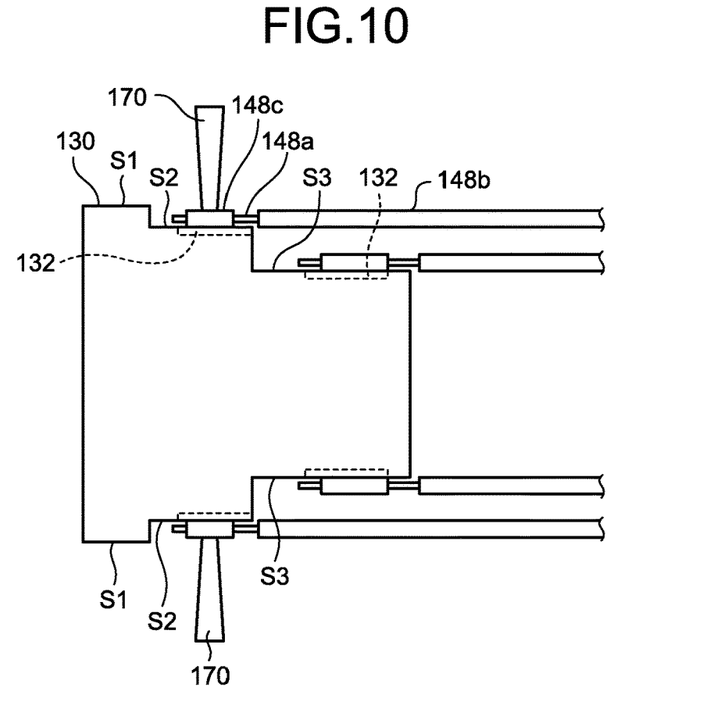
FIG. 10 is a side view that illustrates joining of a signal cable to a connection land.

FIG. 8 is a perspective view of an imaging unit 140 according to a second embodiment of the disclosure. FIG. 9 is an exploded perspective view of the imaging unit 140 of FIG. 8. FIG. 10 is a side view that illustrates joining of a signal cable 148 to a connection land 132.

The imaging unit 140 includes: a semiconductor package 110 in which a cover glass 112 is attached to an imaging element 111 and a sensor electrode 113 is formed on a surface f2 that is the back surface of the imaging element 111; a first circuit substrate 120 having a first electrode pad (not illustrated) and a second electrode pad 122 formed on a surface f3, which is the front surface, and a surface f4, which is the back surface, the first electrode pad on the surface f3 being electrically and mechanically connected to the sensor electrode 113 in the semiconductor package 110; a second circuit substrate 130 having an undepicted third electrode pad formed on a surface f5, which is the front surface, and having connection lands 132 formed on a surface f6 and a surface f7, which are opposed side surfaces, the signal cables 148 being connected thereto; and electronic components 124 mounted on the surface f4 that is the back surface of the first circuit substrate 120.

In the imaging unit 140, the first circuit substrate 120, the second circuit substrate 130, and the signal cables 148 connected to the connection lands 132 on the surface f6 and the surface f7, respectively, are located within the projection plane of the semiconductor package 110 in the optical axis direction.

Light focused by the lens unit enters a light receiving surface f0 of the imaging element 111 via a surface f1 that is the front surface of the cover glass 112. On the surface f2 (the back surface) of the imaging element 111, the sensor electrode 113 and a joint member 114, such as a solder ball, are formed. The joint member 114 may be not only a solder ball but also a metallic cored solder ball, a resin cored solder ball, Au bump, or the like. It is preferable that the semiconductor package 110 is a CSP (chip size package), that is, after an imaging element chip in a wafer state is subjected to wiring, electrode formation, resin sealing, and dicing, the imaging element chip in the size finally becomes the semiconductor package 110 in the same size.

The first circuit substrate 120 is shaped like a plate by laminating multiple substrates with wires formed therein (multiple substrates parallel to the surface f3 and the surface f4 are laminated). Ceramic substrates, glass epoxy substrates, flexible substrates, glass substrates, silicon substrates, or the like, are used as multi-layer substrates. Inside the first circuit substrate 120, a plurality of vias is formed, which allows electrical connection between wires on multi-layer substrates. The first electrode pad is formed on the surface f3 of the first circuit substrate 120, and each is electrically and mechanically connected to the sensor electrode 113 of the semiconductor package 110 via the joint member 114. The part connecting the first electrode pad on the surface f3 and the sensor electrode 113 on the surface f2 is sealed with undepicted sealing resin.

Furthermore, as illustrated in FIG. 9, a recessed portion 121 is provided at the central part of the surface f4 of the first circuit substrate 120, and a mount land 125 for mounting the electronic component 124 is formed within the recessed portion 121. The mounted electronic components 124, illustrated by example, are a passive component such as a capacitor or a resistance coil, and an active component such as a driver IC. Mounting the electronic components 124 within the recessed portion 121 near the center of the first circuit substrate 120 enables a short distance between the imaging element 111 and the electronic components 124 and low impedance and achieves stable driving of the imaging element 111, whereby high-quality images may be obtained. The second electrode pad 122 is formed on the surface f4 of the first circuit substrate 120 at areas other than the recessed portion 121, and it is electrically and mechanically connected to the third electrode pad on the surface f5 of the second circuit substrate 130 described later via a joint member 123.

The second circuit substrate 130 is a lamination of substrates with wires formed therein, formed of a ceramic substrate, glass epoxy substrate, glass substrate, silicon substrate, or the like, and is a deformed substrate in which the surface f6 and the surface f7 (side surfaces) opposed to each other are arranged in a stepped pattern.

As illustrated in FIG. 9, the third electrode pad to be connected to the second electrode pad 122 is formed on the surface f5, which is the front surface of the second circuit substrate 130.

The surface f6 and the surface f7, which are side surfaces of the second circuit substrate 130, have a stepped pattern such that they are located close to each other at the proximal end side of the semiconductor package 110 in the optical axis direction, that is, the surface f6 and the surface f7 are provided with stepped portions S1, S2, and S3.

The connection lands 132 are formed on the stepped portions S2 and S3 of the surface f6 and the surface f7. The connection lands 132 on the stepped portions S2 and S3 are provided such that they are misaligned so as not to be overlapped in the optical axis direction. An outer surface 148*b* of the signal cable 148 at one end is removed, and an exposed core 148*a* is covered with a metallic tube 148*c*. The metallic tube 148*c* to be used may be the same as the metallic tube 48*c* according to the first embodiment.

According to the second embodiment, the connection lands 132 are formed on the surface f6 and the surface f7, opposed to each other, of the second circuit substrate 130, and the signal cables 148 are connected; therefore, as illustrated in FIG. 10, it is preferable that the cores 148*a* covered with the metallic tubes 148*c* are placed on the connection lands 132 on the stepped portions S2 of the surface f6 and the surface f7, they are simultaneously sandwiched with an ultrasound horn 170 in a vertical direction and, in a pressed state, vibrations are applied for ultrasound joining. Simultaneous joining in a vertical direction allows high-efficient application of pressure and ultrasound vibrations. In the same manner, ultrasound joining may be applied for the connection to the connection lands 132 on the stepped portion S3. Due to ultrasound joining, an indentation 148d is formed on the metallic tube 148c.

For joining between the core 148a and the connection land 132 with solder, even with use of the thinnest solder iron (the distal-end diameter of 0.2 mm, the tapered form of the thinnest distal end), it is difficult to make a connection to the connection lands 132 (the smallest connection land 132: a length of 0.4 mm, a width of 0.1 mm, a pitch of 0.2 mm in the case of solder connection) on the stepped portions S2 and S3, especially a connection near a stepped part. However, for ultrasound joining, the distal end diameter of the ultrasound horn 170 may be approximately several dozens of μm, which allows easy joining even near a stepped part and a shorter length of the second circuit substrate 130 in the optical axis direction.

Furthermore, according to the second embodiment, in the same manner as the first embodiment, during joining, the core 148a is covered with the metallic tube 148c having a diameter larger than that of the core 148a; therefore, the target to be joined is large, and a joining task is easy. Furthermore, the metallic tube 148c prevents thin wires from being unjoined so as to avoid the occurrence of short circuits, and the like.

Figure 11:
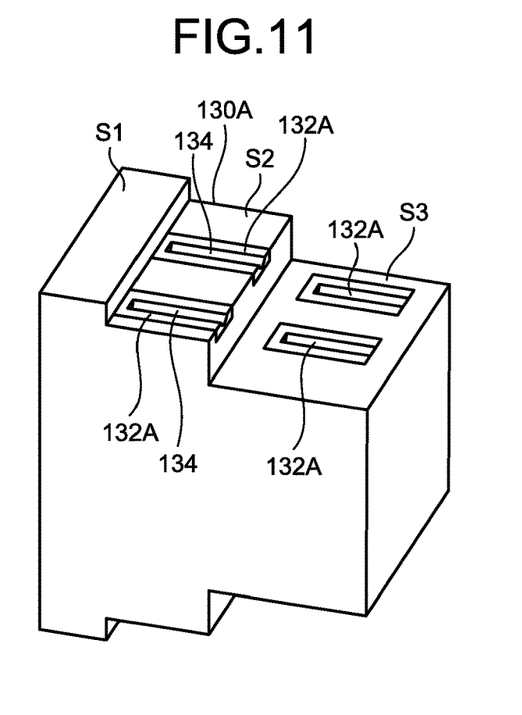
FIG. 11 is a perspective view of a second circuit substrate according to a modification of the second embodiment of the disclosure.
Figure 12:
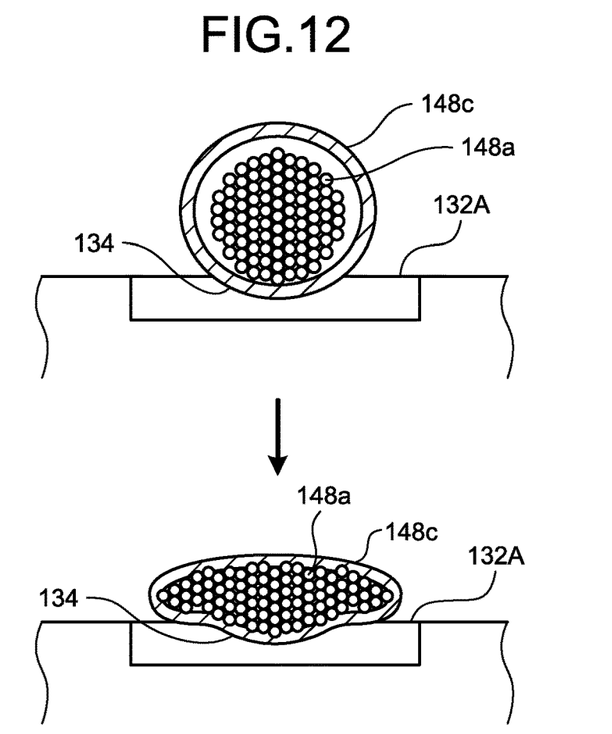
FIG. 12 is a cross-sectional view that illustrates joining of the signal cable to a connection land according to the modification of the second embodiment of the disclosure.

Furthermore, the connection land 132 may be provided with a groove. FIG. 11 is a perspective view of a second circuit substrate 130A according to a modification of the second embodiment of the disclosure. FIG. 12 is a cross-sectional view that illustrates joining of the signal cable 148 to a connection land 132A according to the modification of the second embodiment of the disclosure.

In the second circuit substrate 130A, the connection land 132A is provided with a groove 134 that is parallel to the optical axis direction. The groove 134 is an interlayer via portion in a multi-layer substrate that forms the second circuit substrate 130A. Formation of the groove 134 on the connection land 132A improves the stability of the cylindrical metallic tube 148c to be placed, increases the contact area between the connection land 132A and the metallic tube 148c (the core 148a), and enhances the conductivity and the reliability of a connection.

Third Embodiment

Figure 13:
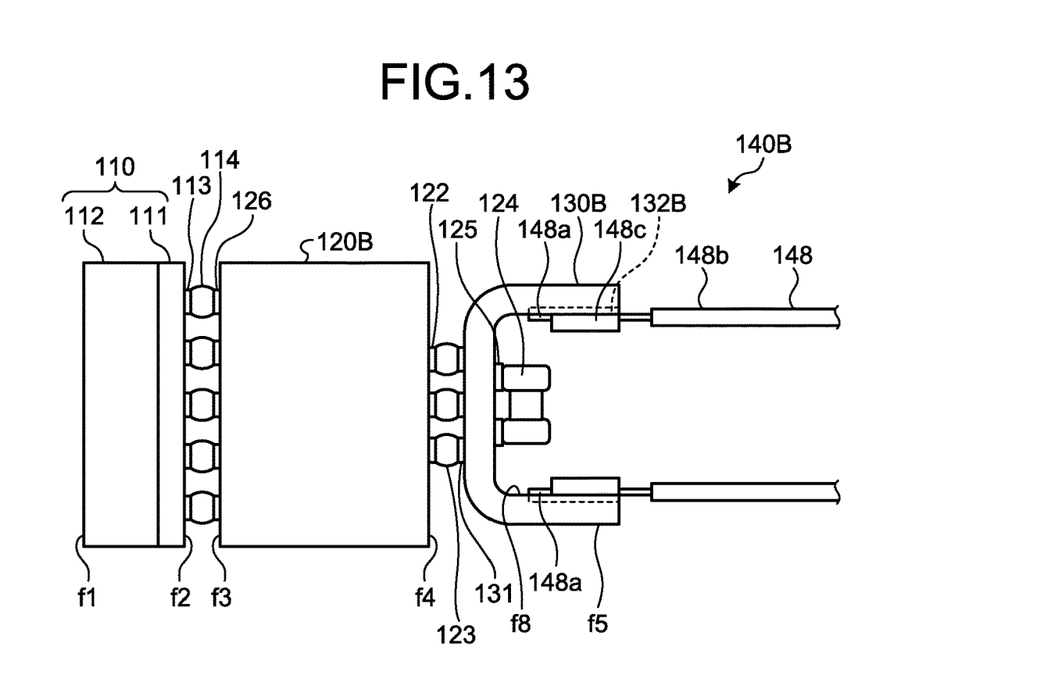
FIG. 13 is a side view of an imaging unit according to a third embodiment of the disclosure.

FIG. 13 is a side view of an imaging unit 140B according to a third embodiment of the disclosure.

The imaging unit 140B includes: the semiconductor package 110; a first circuit substrate 120B having a first electrode pad 126 and the second electrode pad 122 formed on the surface f3, which is the front surface, and the surface f4, which is the back surface, respectively, the first electrode pad 126 on the surface f3 being electrically and mechanically connected to the sensor electrode 113 in the semiconductor package 110; a second circuit substrate 130B having a third electrode pad 131 formed on the surface f5, which is the front surface, and having a connection land 132B for connecting the signal cable 148 formed on a surface f8, which is the back surface; and the electronic component 124 mounted on the surface f8, which is the back surface of the second circuit substrate 130B.

The first circuit substrate 120B is shaped like a plate by laminating multiple substrates with wires formed therein (multiple substrates parallel to the surface f3 and the surface f4 are laminated). Ceramic substrates, glass epoxy substrates, flexible substrates, glass substrates, silicon substrates, or the like, are used as multi-layer substrates. Inside the first circuit substrate 120B, a plurality of vias is formed, which allows electrical connection between wires on multilayer substrates.

The second circuit substrate 130B is an FPC substrate. The third electrode pad 131 is formed at the side of the surface f5, which is the front surface, at the center part of the second circuit substrate 130B, and the mount land 125 for connecting the electronic component 124 is formed at the side of the surface f8, which is the back surface, at the central part. Furthermore, a connection land (not illustrated) for connecting the signal cable 148 is formed on both sides of the mount land 125 of the second circuit substrate 130B. After the second circuit substrate 130B has the electronic component 124 mounted thereon and has the core 148a of the signal cable 148 joined thereto via the metallic tube 148c with ultrasound waves, it is bent in a C shape such that the signal cable 148 extends in the optical axis direction. By bending the second circuit substrate 130B, the second circuit substrate 130B and the signal cable 148 are located within the projection plane of the semiconductor package 110 in the optical axis direction. Here, the first circuit substrate 120B is also located within the projection plane of the semiconductor package 110 in the optical axis direction.

According to the third embodiment, after the signal cable 148 is joined to the second circuit substrate 130B with ultrasound waves via the metallic tube 148c, the first circuit substrate 120B and the second circuit substrate 130B get connected to each other. Joining of the signal cable 148 to the connection land on the second circuit substrate 130B, which is an FPC substrate, may be easily conducted as compared with joining to the second circuit substrate 130, which is a deformed substrate, according to the second embodiment as the connection land is formed only on the surface f8, the back surface, and it is conducted before connection to the first circuit substrate 120B. Here, connection lands may be formed on two sides (the surface f5 and the surface f8) of the second circuit substrate 130B so as to improve the mounting density of the signal cables 148.

Furthermore, according to the third embodiment, in the same manner as the first and the second embodiments, during joining, the core 148a is covered with the metallic tube 148c having a diameter larger than that of the core 148a; therefore, the target to be joined is large, and a joining task is easy. Furthermore, the metallic tube 148c prevents thin wires from being unjoined so as to avoid the occurrence of short circuits, and the like.

Figure 14:
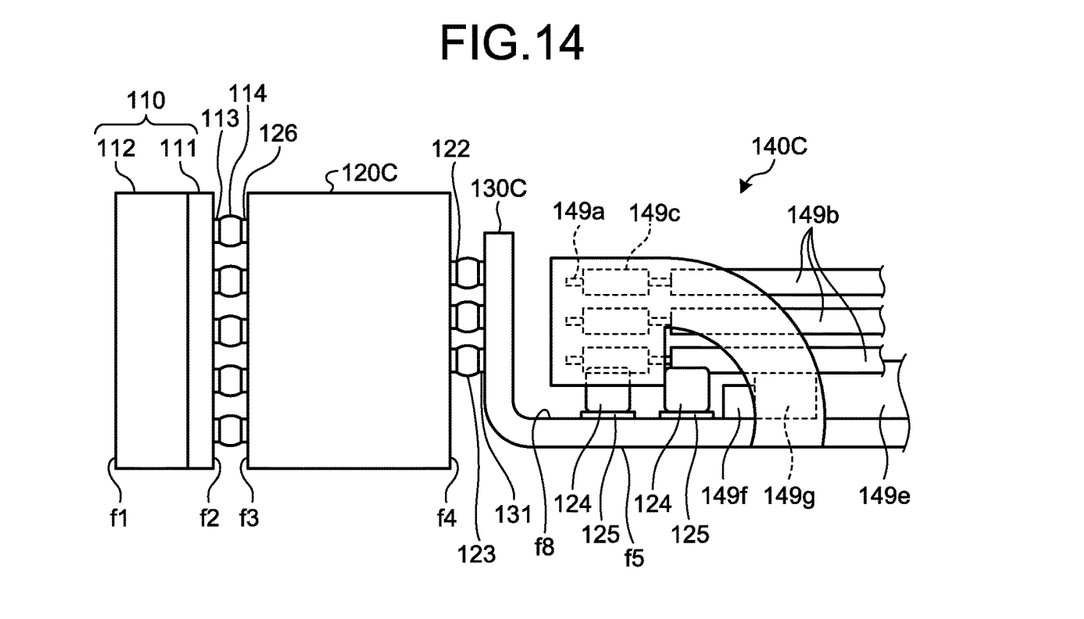
FIG. 14 is a side view of an imaging unit according to a modification of the third embodiment of the disclosure.
Figure 15:
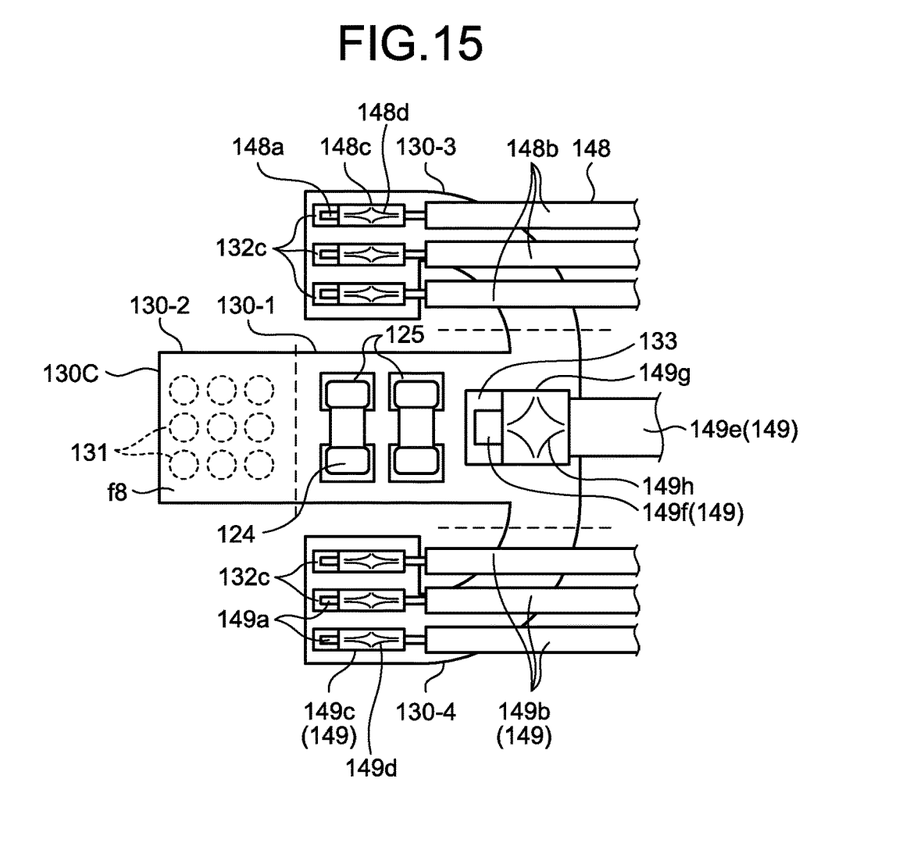
FIG. 15 is a development view of a second circuit substrate used in the imaging unit of FIG. 14.

According to the above-described third embodiment, the second circuit substrate 130B is bent in a C shape so that the second circuit substrate 130B and the signal cable 148 fall within the projection plane of the semiconductor package 110 in the optical axis direction, and the signal cable 148 extends in the optical axis direction; however, this is not a limitation. FIG. 14 is a side view of an imaging unit 140C according to a modification of the third embodiment of the disclosure. FIG. 15 is a development view of a second circuit substrate 130C used in the imaging unit 140C of FIG. 14.

The second circuit substrate 130C is an FPC substrate including a first area 130-1, a second area 130-2, a third area 130-3, and a fourth area 130-4.

On the back surface f8 of the first area 130-1, the mount land 125 for mounting the electronic component 124 and a connection land 133 for connecting a shield 149f of a coaxial cable 149 are formed. The first area 130-1 is arranged parallel to the optical axis direction. An outer surface 149e of the shield 149f of the coaxial cable 149 is removed, and it is inserted into the opening portion of a metallic tube 149g in a bundle. The shield 149f is joined to the connection land 133 with ultrasound waves via the metallic tube 149g. Due to ultrasound joining, an indentation 149h is formed on the metallic tube 149g.

The third electrode pad 131 connected to the second electrode pad 122 on a first circuit substrate 120C is formed on the front surface f5 of the second area 130-2. The second area 130-2 is bent such that it is perpendicular to the optical axis direction and the first area 130-1.

A connection land 132c for connecting the core 148a of the signal cable 148 (single wire) is formed on the back surface f8 of the third area 130-3. The third area 130-3 is bent such that it is parallel to the optical axis direction and is perpendicular to the first area 130-1. The core 148a of the signal cable 148 is joined to the connection land 132c with ultrasound waves via the metallic tube 148c. Due to ultrasound joining, the indentation 148d is formed on the metallic tube 148c. The connection land 132c is formed such that its longitudinal direction is parallel to the optical axis direction and, when the third area 130-3 is bent, the joined signal cable 148 extends in the optical axis direction.

The connection land 132c for connecting a core 149a of the coaxial cable 149 is formed on the back surface f8 of the fourth area 130-4. The fourth area 130-4 is bent such that it is parallel to the optical axis direction and the third area 130-3 and is perpendicular to the first area 130-1. The core 149a of the coaxial cable 149, with an internal insulating material 149b removed therefrom, is inserted into the opening portion of a metallic tube 149c. The core 149a is joined to the connection land 132c with ultrasound waves via the metallic tube 149c. Due to ultrasound joining, an indentation 149d is formed on the metallic tube 149c. The connection land 132c is formed such that its longitudinal direction is parallel to the optical axis direction and, when the fourth area 130-4 is bent, the core 149a of the joined coaxial cable 149 extends in the optical axis direction. Here, the metallic tubes 149c and 149g are made of the material identical to that of the metallic tube 148c, and the diameter of the opening portion thereof may be appropriately determined in consideration of the outer diameter of the core 149a and the shield 149f inserted, respectively.

By bending the second circuit substrate 130C as described above, the second circuit substrate 130C, the signal cable 148, and the coaxial cable 149 are located within the projection plane of the semiconductor package 110 in the optical axis direction. Here, the first circuit substrate 120C is also located within the projection plane of the semiconductor package 110 in the optical axis direction.

According to the modification of the third embodiment, in the same manner as the third embodiment, after the signal cable 148 and the coaxial cable 149 are joined to the second circuit substrate 130C via the metallic tubes 148c, 149c, and 149g with ultrasound waves, the first circuit substrate 120C and the second circuit substrate 130C get connected to each other. Joining of the signal cable 148 and the coaxial cable 149 to the connection lands 132c, 133 on the second circuit substrate 130C, which is an FPC substrate, may be easily conducted as compared with joining to the second circuit substrate 130, which is a deformed substrate, according to the second embodiment as the connection lands 132c, 133 are formed on only the back surface f8 and it is conducted before connection to the first circuit substrate 120C.

According to some embodiments, even when extremely thin signal cables are used, high reliability of a connection and a short interval at which connection lands are disposed are achieved, whereby it is possible to reduce the size of the electronic circuit unit, the imaging unit, and the endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electronic circuit unit comprising:
    a cable having a core of stranded thin wires, the core being covered with an outer surface, the outer surface at one end of the cable being removed to expose the core;
    a metallic tube that is tubular, the exposed core being inserted into an opening portion of the metallic tube; and
    a substrate including a connection land for connecting the core, wherein
    the exposed core is connected to the connection land via the metallic tube by diffusion joining or ultrasound joining,
    the core has a diameter of 0.02 to 0.50 mm,
    the metallic tube has a thickness of 10 to 50 μm, and
    the metallic tube has an inner diameter that is larger than the diameter of the core by equal to or more than 1.1-fold and equal to or less than by 1.5-fold.

2. The electronic circuit unit according to claim 1, wherein the metallic tube is made of a material identical to a material with which a surface of the connection land is formed.

3. The electronic circuit unit according to claim 1, wherein the metallic tube is made of a material having a lower degree of hardness than a material of the core.

4. The electronic circuit unit according to claim 1, wherein the metallic tube has a cylindrical shape.

5. The electronic circuit unit according to claim 1, wherein the metallic tube is made of gold and is formed by a plating technique.

6. The electronic circuit unit according to claim 1, wherein the connection land is provided with a groove.

7. An imaging unit comprising:
    an imaging element configured to receive light and conduct photoelectric conversion to generate an electric signal; and
    the electronic circuit unit according to claim 1.

8. The imaging unit according to claim 7, further comprising a flexible printed substrate extending from the imaging element in an optical axis direction of the imaging element, wherein
    a substrate included in the electronic circuit unit is a multi-layer substrate formed on a surface of the flexible printed substrate, and an electronic component is mounted on the multi-layer substrate, and
    the electronic circuit unit and the electronic component are located within a projection plane of the imaging element in the optical axis direction.

9. The imaging unit according to claim 7, further comprising a circuit substrate connected to a sensor electrode via a first electrode pad and having an electronic component mounted on the circuit substrate, the sensor electrode being formed on a back surface of the imaging element, wherein a substrate included in the electronic circuit unit is a deformed substrate connected to a second electrode pad formed on a back surface of the circuit substrate, and the electronic circuit unit is located within a projection plane of the imaging element in the optical axis direction.

10. The imaging unit according to claim 7, further comprising a circuit substrate connected to a sensor electrode via a first electrode pad the sensor electrode being formed on a back surface of the imaging element, wherein a substrate included in the electronic circuit unit is a flexible printed substrate connected to a second electrode pad formed on a back surface of the circuit substrate, an electronic component being mounted on the flexible printed substrate, and the electronic circuit unit and the electronic component are located within a projection plane of the imaging element in the optical axis direction.

11. An endoscope comprising an insertion portion having a distal end provided with the imaging unit according to claim 7.

\* \* \* \* \*